United States Patent
Deluca (10) Patent No.: US 6,306,406 B1
(45) Date of Patent: Oct. 23, 2001

(54) DRUG DELIVERY SYSTEM INVOLVING INTERACTION BETWEEN PROTEIN OR POLYPEPTIDE AND HYDROPHOBIC BIODEGRADABLE POLYMER

(75) Inventor: Patrick P. Deluca, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 08/481,155

(22) Filed: Jun. 7, 1995

Related U.S. Application Data (63) Continuation of application No. 07/865,657, filed on Apr. 7, 1992, now abandoned, which is a continuation of application No. 07/716,763, filed on Jun. 19, 1991, now abandoned, which is a continuation of application No. 07/554,427, filed on Jul. 19, 1990, now abandoned.

(51) Int. Cl.$^7$ ................................ A61K 9/00; A61K 9/50
(52) U.S. Cl. ............................................ 424/400; 424/499
(58) Field of Search ................................... 429/400, 499

(56) References Cited

U.S. PATENT DOCUMENTS

| | | | |
|---|---|---|---|
| 3,773,919 | * 11/1973 | Boswell et al. | 424/501 |
| 3,843,446 | 10/1974 | Vieth et al. | |
| 3,972,776 | 8/1976 | Vieth et al. | |
| 3,977,941 | 8/1976 | Vieth et al. | |
| 4,494,994 | 1/1985 | Cioca et al. | |
| 4,557,855 | 12/1985 | Cioca et al. | |
| 4,585,797 | 4/1986 | Cioca. | |
| 4,591,501 | 5/1986 | Cioca. | |
| 4,601,981 | 7/1986 | Vieth et al. | |
| 4,741,872 | * 5/1988 | DeLuca et al. | 424/501 |
| 4,758,342 | 7/1988 | Heckmann et al. | |
| 4,818,542 | * 4/1989 | Deluca et al. | 424/491 |
| 4,857,311 | * 8/1989 | Domb et al. | 528/271 |
| 4,863,735 | * 9/1989 | Kohn et al. | 424/422 |
| 4,871,716 | * 10/1989 | Fongo et al. | 424/501 |
| 4,873,033 | 10/1989 | Heckmann et al. | |
| 4,897,444 | 1/1990 | Brynes et al. | |
| 4,962,091 | * 10/1990 | Eppstein et al. | 424/499 |
| 5,004,602 | * 4/1991 | Hutchinson | 424/499 |
| 5,008,116 | 4/1991 | Cahn. | |
| 5,019,400 | * 5/1991 | Gombotz et al. | 424/499 |
| 5,366,734 | * 11/1994 | Hutchinson | 424/426 |

FOREIGN PATENT DOCUMENTS

| | | |
|---|---|---|
| 0 058 481 | 8/1982 | (EP). |
| 0058481 | * 8/1982 | (EP). |
| 0 187 547 | 7/1986 | (EP). |
| 0 245 820A3 | 11/1987 | (EP). |
| 0330180 | * 8/1989 | (EP). |
| 0 330 180 | 8/1989 | (EP). |
| 0 354 714 | 2/1990 | (EP). |
| 2 207 050 A | 1/1989 | (GB). |
| 2209937 | * 1/1989 | (GB) ................................. 424/499 |
| 203299 | 2/1983 | (NZ). |
| 220969 | 6/1987 | (NZ). |
| 221411 | 8/1987 | (NZ). |
| 223843 | 3/1988 | (NZ). |
| 88/09664 | 12/1988 | (WO). |
| 91/06286 | 5/1991 | (WO). |

OTHER PUBLICATIONS

Wakiyama et al Chem. Pharm. Bull. No. 7 pp. 2621–2628.*
Yoshioka, T., Hashida, M., Muranishi, S., and Sezaki, H., Intern. J. Pharm., 81, 131 (1981), "Specific Delivery of Mitomycin C. to Liver, Spleen and Lung: Nano–and Microspherical Carriers of Gelatin.".
Wakiyama, N., Kaxuhiko, J., Nakano, M., Chem. Pharm. Bull., 30, 2621 (1982), "Influence of Physicochemical Properties of Polylactic Acid on the Characteristics and In Vitro Release Patterns of Polylactic Acid Microspheres Containing Local Anesthetics."

* cited by examiner

Primary Examiner—Thurman K. Page
Assistant Examiner—T. Ware
(74) Attorney, Agent, or Firm—Burns, Doane, Swecker & Mathis, LLP (57) ABSTRACT

A drug delivery system for controlled release of a protein or polypeptide comprising a hydrophobic biodegradable polymer and a protein or polypeptide. A physical interaction is present between the polymer and the protein or polypeptide, thus, allowing protection and controlled release of the protein or polypeptide in-vivo. The drug delivery system may be prepared by a polymer precipitation technique or a microsphere technique.

15 Claims, 7 Drawing Sheets

PRECIPITATION METHOD

```
Salmon Calcitonin         Polymer
         \                  /
          \                /      Aqueous Buffer
           \              /            or
            Dissolved in  ←──── Alcoholic
              Solvent              Solution
                │
        Polymer Precipitate
        Containing Calcitonin
                │
            Filtration
                │
               Dry
```

DRUG DELIVERY SYSTEM INVOLVING INTERACTION BETWEEN PROTEIN OR POLYPEPTIDE AND HYDROPHOBIC BIODEGRADABLE POLYMER

This application is a continuation of application Ser. No. 07/865,657, filed Apr. 7, 1992, now abandoned; which is a continuation of application Ser. No. 07/716,763, filed Jun. 19, 1991 (now abandoned); which is a continuation of application Ser. No. 07/554,427, filed Jul. 19, 1990 (now abandoned).

BACKGROUND OF THE INVENTION

(1) Field of the Invention

The present invention relates generally to the field of biodegradable polymers for the controlled release of biologically active agents therefrom. More particularly, the present invention relates to a process for preparing hydrophobic biodegradable polymers of controlled size in which there is a physical interaction with the protein or polypeptide incorporated therein. Such an interaction promotes incorporation of the protein or polypeptide into the polymer matrix and allows for protection and controlled release of the protein or polypeptide from the polymer.

(2) Background of the Prior Art

A wide variety of microencapsulation drug delivery systems have been developed heretofore for the rate controlled release of therapeutic agents or other agents. For instance, considerable research has been devoted to incorporating therapeutic agents into polyesters such as poly-$\epsilon$-caprolactone), poly($\epsilon$-caprolactone-Co-DL-lactic acid), poly (DL-lactic acid), poly(DL-lactic acid-Co-glycolic acid) and poly($\epsilon$-caprolactone-Co-glycolic acid) in which release was diffusion controlled. See, for example, Pitt, C. G., Gratzl, M. M., Jeffcoat, A. R., Zweidinger, R., Schindler, A., "Sustained Drug Delivery Systems. II. Factors Affecting Release Rates from Poly($\epsilon$-caprolactone) and Related Biodegradable Polyesters", *J. Pharm. Sci.*, 68, 1534 (1979). These systems were fabricated as films and capsules and the results suggest that the devices can be prepared to erode after release of the drug is essentially complete. Degradation of the polyesters has been reported to proceed by random hydrolytic cleavage of ester linkages by an autocatalytic process with the rate of chain cleavage being influenced by chemical and morphological factors.

Sustained release systems of antimalarial agents and sulfadiazine in glycolic-lactic acid copolymers have also been reported. Wise, D. L., Gesser, J. D., McCormick, G. J., "Sustained Release of a Dual Anti-malarial System", *J. Pharm. Pharmacol.*, 31, 201 (1979). Wise, D. L., McCormick, G. J., Willett, G. P., Anderson, L. C., Howes, J. F., *J. Pharm. Pharmacol.*, 30, 686 (1978). Methods reported by the foregoing investigators involved dissolving the agents in a suitable solvent and either spray drying or casting films according to usual methods and evaporating the solvent. Various narcotic antagonists and steroids have been incorporated in films and implanted in rats (e.g., see Woodland, J. H. R., Yolles, S., Blake, D. A., Helrich, M., Meyer, F. J., "Long-Acting Delivery Systems for Narcotic Antagonists: I", *J. Med. Chem.*, 16, 897 (1973), Jackanicz, T. M., Nash, H. A., Wise, D. L., Gregory, J. B., "Polylactic Acid as a Biodegradable Carrier for Contraceptive Steroids", *Contraception*, 8, 227 (1973). Anderson, L. C., Wise, D. L., Howes J. F., "An Injectable Sustained Release Fertility Control System", *Contraception*, 13, 375 (1976) and incorporated into particles injected subcutaneously [Yolles, S., "Time-Release Depot for Anticancer Drugs: Release of Drugs Covalently Bonded to Polymers", *J. Parent. Drug Assoc.*, 32, 188(1978)]. The release of a number of anti-tumor agents has been evaluated in implantable systems as reported in [Yolles, S., "Time Release Depot for Anticancer Drugs: Release of Drugs Covalently Bonded to Polymers", *J. Parent. Drug Assoc.*, 32, 188 (1978)], and the antibiotic Mitomycin C has been encapsulated in microspherical carriers of gelatin and administered intravenously [Yoshioka, T., Hashida, M., Muranishi, S., and Sezaki, H., "Specific Delivery of Mitomycin C. to Liver, Spleen and Lung: Nano- and Microspherical Carriers of Gelatin", *Intern. J. Pharm.*, 81, 131 (1981)] and the effect of size on in vivo distribution and the potential for antibiotic targeting was discussed. The size distribution of the microspheres (i.e., 5 to 30 $\mu$m) reported in the last mentioned publication was very broad, especially for intravenous administration. Recently the in-vitro release of local anesthetics from polylactic acid spheres prepared by a solvent evaporation process has, likewise, been reported [Wakiyama, N., Kaxuhiko, J., Nakano, M., "Influence of Physicochemical Properties of Polylactic Acid on the Characteristics and In Vitro Release Patterns of Polylactic Acid Microspheres Containing Local Anesthetics", *Chem. Pharm. Bull.*, 30, 2621 (1982)]. The patterns of release from these polylactic acid spheres were characterized by the various degrees of degradation of the polymer as well as solubilities of loaded drugs, although no attempt was apparently made to evaluate this parameter. Additionally, it is apparent that the solubility of the drug played an important role in the rate and extent of release. Scanning electron photomicrographs also revealed varying degrees of erosion and deformation of the spheres after release.

It will be seen from the foregoing that while the controlled release delivery of pharmaceuticals or other agents from heretofore described polymeric systems has been principally limited to oral, topical or implantable systems in which the considerations relative to pore size and/or cell size within the carrier matrix as well as the overall dimensions of the microspheres to be administered along with the rate of release and the relative absorption rate from a bioavailability standpoint are distinctly different from the evaluation parameters involved in the utilization of these microsphere delivery systems for parenteral, i.e., intravenous, intraarterial, intramuscular, subcutaneous, intraocular or inhalation administration routes to which the present invention is particularly applicable.

For instance, U.S. Pat. No. 4,818,542 describes a controlled release drug delivery system comprised of a spherical microprocess polymeric network of interconnecting channels.

Further, the use of proteins and peptides as therapeutic agents has been recognized and their position within the pharmaceutical armamentarium is growing due to their increasing availability. This availability is primarily due to recent advances in genetic engineering and biotechnology. Unfortunately, the use of proteinaceous drugs by conventional routes of administration is generally hampered by a variety of delivery problems. Nonparenteral routes of administration, i.e., oral and percutaneous, are inefficient primarily due to poor absorption of proteinaceous drugs into the bloodstream and degradation of such drugs in the gastrointestinal tract. Rapid proteolytic inactivation of the proteinaceous drug also occurs when the drug is administered parenterally thus decreasing its bioavailability. In addition, when administered by the parenteral route, the host's immune system is activated thereby potentially setting off a series of undesirable immune reactions.

In view of the foregoing, considerable effort has been devoted to developing alternative systems for parenteral delivery of peptides and proteins to obviate the problems associated with prior art administration techniques. For instance, implantable devices have been cast or molded from poly-(hydroxy-ethyl)methacrylate, polyvinyl alcohol, ethylene-vinylacetate copolymer (EVA) and silicone elastomer. Macromolecular drugs have been embedded in those devices. A typical method of preparation involves suspending a powder of a macromolecular drug such as a solid protein or peptide in a solution containing the polymer. The entire composition is then case or molded into the desired size and shape either by evaporating the solvent or by vulcanization. A sustained release of macromolecules from these devices has been demonstrated. The simplicity of the foregoing prior art method is its primary advantage.

To avoid the foregoing difficulties, U.S. Pat. No. 4,741,872 discloses a method for preparing biodegradable microspheres having a three-dimensional network in which biologically active macromolecular agents are physically entrapped therein.

A number of other types of protein/polymer systems are known in the art. For instance, U.S. Pat. Nos. 3,843,446, 3,977,941 and 4,601,981 discloses the preparation of enzymatically active protein-enzyme complex membrane by treating another protein membrane with an aqueous solution of an enzyme. The membranes are used to effect enzymatic reactions.

U.S. Pat. No. 3,972,776 discloses the preparation of enzymatically active protein-whole microbial cell complex membranes suitable for effecting enzymatic reactions by forming a dispersion containing synthetic or natural protein macromolecules and whole microbial cells, casting a membrane from the dispersion and drying the membrane. The membranes may also be formed by electro-codeposition from a dispersion containing the macromolecular and cells.

U.S. Pat. No. 4,758,342 relates to a hyperfiltration membrane containing a supporting layer and a separation layer.

U.S. Pat. Nos. 4,494,944 and 4,557,855 disclose a surface active agent comprised of lignin sulfonic acids, and optionally, an alkylaryl sulfonic free acid with at least ten carbon atoms and eight polypeptides having a molecular weight of about 2,500 to about 15,000.

U.S. Pat. Nos. 4,585,787 and 4,591,501 disclose a flexible continuous film which is comprised of a physical admixture of a polypeptide, a plasticizer and a film-forming flexible polymer, when the film is moistened, the polypeptide exudes therefrom.

U.S. Pat. No. 4,873,033 relates to a hyperfiltration membrane containing a supporting layer and a separation layer. The separation layer consists of a crosslinked monomolecular film of molecules, the molecules of the separation layer in the uncrosslinked state being surfactants or surfactant-like lipoids containing at least one hydrophobic chain and at least one hydrophilic group. The surfactant-like lipoid molecules are spread out under a certain spreading pressure or occupy an average space over the surface of an aqueous solution or at the interface between an aqueous solution and a liquid immersible therewith.

U.S. Pat. No. 4,897,444 relates to an immobilized fluorogenic substrate. The substrate has the structure wherein $R_1$ represents an enzyme-specific oligopeptide, $R_2$ represents a spacer group which is a methylene- carboxyloxy, a methylene carboxamido or a methylene-sulfonamido group attached to a polymethylene chain which itself has a functional group suitable for coupling with a polymer; $R_3$ represents a biologically inert polymer; and $R_4$ represents a fluorogenic moiety.

GB 2 207 050 discloses a composition comprising an aqueous solution of a drug and a glucose polymer mixture which includes at least 50% by weight of glucose polymers of D.P. greater than 12. The composition is introduced into the peritoneal cavity. The glucose polymers act as osmotic agents during peritoneal dialysis.

EP 0 354 714 discloses a pharmaceutical composition for affecting tissue redistribution of bioactive peptides and proteins which are normally bound to glycoaminoglycans, and for mimicking the action of glycoaminoglycans in biological interactions. The composition comprises a pharmaceutically acceptable polymeric compound having monomeric units and a molecular weight between 1,000 and 20,000 Daltons, wherein each monomeric unit contains between three and about 10 aromatic rings.

EP 0 187 547 relates to polymeric drugs comprising an inert synthetic polymeric carrier covalently attached to low molecular weight bioactive molecules. Drug delivery is somewhat targeted because uptake is restricted to cells capable of a substrate selective mechanism known as pinocytosis.

In spite of the numerous teachings of the prior art, the prior art drug delivery systems still have some significant disadvantages and commercialization has been difficult to achieve especially with respect to sufficient drug loading, reproducibility of product specifications and scale-up.

SUMMARY OF THE INVENTION

It is, therefore, the object of this invention to provide one or more processes for the incorporation of polypeptides and proteins into a hydrophobic biodegradable polymer to provide a stable formulation and to achieve protection and controlled release of the polypeptide or protein from the polymer in vivo.

It is another object of the present invention to provide for a drug delivery system itself which allows for controlled release of the polypeptide or protein from the polymer in vivo, wherein said incorporation, protection and controlled release are due to the physical interaction between the polypeptide or protein and the hydrophobic biodegradable polymer.

A still further object of the present invention is to provide a microspherical drug delivery system which allows targeting of drugs or other agents to specific host tissues or cells via injection or inhalation providing high localized concentrations, sustained activity, systemic administration and treatment, thereby minimizing undesirable systemic effects of toxic drugs administered in the native form.

These and similar objects, advantages and features are accomplished according to the methods and compositions of the following description of the present invention.

DESCRIPTION OF THE PREFERRED EMBODIMENTS OF THE INVENTION

A variety of hydrophobic biodegradable polymers are suitable in the drug delivery system of the present invention. Such polymers are well-known to those of ordinary skill in this art. Suitable polymers include polyesters, polyorthoesters and polyanhydrides.

The polymer may comprise copolymeric and homopolymeric polyesters containing hydrolyzable inter linkages which are, therefor, biodegradable. Typically preferred of such polyesters are polyglycolic (PGA) and polylactic (PLA) acids, and copolymers of glycolide and L-lactide (PGL). The aforementioned polyesters are particularly suited for the methods and compositions of the present invention by reason of their characteristically low human toxicity and virtually complete biodegradability. of course, it will be understood that the particular polyester or other polymer, oligomer, copolymer, and the like, utilized in the present invention is not critical and a variety of hydrophobic biodegradable polymers may be utilized as a consequence of the novel processing methods of the invention which yield the desired drug delivery system, irrespective of the source of polymer utilized.

Accordingly, other biodegradable or bioerodable polymers or copolymers evidencing the necessary low degree of toxicity suitable for use in the present invention include, for example, gelatin, agar, starch, arabinogalactan, albumin, collagen, natural and synthetic materials or polymers, such as poly($\epsilon$-caprolactone), poly($\epsilon$-caprolactone-Co-lactic acid), poly($\epsilon$-caprolactone-Co-glycolic acid), poly($\beta$-hydroxy butyric acid), polyethylene oxide, polyethylene, poly(alkyl-2-cyanoacrylate), (e.g., methyl, ethyl, butyl, and the like), hydrogels (e.g., poly(hydroxyethyl methacrylate poly-hydroxyethyl methacrylate), polyamides (e.g., polyacrylamide), poly(amino acids)(i.e., L-leucine, L-aspartic acid, $\beta$-methyl-L-aspartate, $\beta$-benzyl-L-aspartate, glutamic acid and the like), poly(2-hydroxyethyl-DL-aspartamide), poly(ester urea), poly(L-phenylalanine/ethylene glycol/1,6-diisocyanatohexane), poly(methyl methacrylate), 3,9-bis methylene-2,4,8,10-tetraoxaspirol [5,5] undecane, 1,6-hexadiol polyorthoester, poly(bis-p-carboxyphenoxypropane anhydride), ethylene-vinylacetate copolymer (EVA), polyvinyl alcohol (PVA) and silicone elastomer.

The foregoing exemplary natural and synthetic polymers suitable for use in the present invention are, of course, either readily available commercially or are obtainable by condensation polymerization reactions from the suitable monomers or, comonomers or oligomers. For instance, homopolymers and copolymers of glycolic and lactic acids can be prepared by direct poly-condensation or by reacting glycolide and lactide monomers as disclosed by Gilding, D. K., Reed, A. M., "Biodegradable Polymers for Use in Surgery—Polyglycolic/Poly(lactic acid) Homo- and Copolymers: 1", Polymer, 20, 1459 (1979).

Any protein or polypeptide is suitable in the practice of the present invention. Biologically active proteins or polypeptides for use in the present invention are proteins or polypeptides of relatively small molecular weights. Exemplary preferred biologically active polypeptides for use herein are calcitonin, insulin, angiotensin, vasopressin, desmopressin, LH-RH (luteinizing hormone-releasing hormone), somatostatin, glucagon, somatomedin, oxytocin, gastrin, secretin, h-ANP (human atrial natriuretic polypeptide), ACTH (adrenocorticotropic hormone), MSH (melanocyte stimulating hormone), beta-endorphin, muramyl dipeptide, enkephalin, neurotensin, bombesin, VIP, CCK-8, PTH (parathyroid hormone), CGRP (calcitonin gene related peptide), endothelin, TRH (thyroid releasing hormone), growth hormones like erythropoietin, lymphokines like macrophage stimulating factor, and the like. The various polypeptides for use herein include not only the naturally occurring polypeptides themselves but also pharmacologically active derivatives and analogs thereof. Thus, for example, calcitonin intended for use in the present invention includes not only naturally occurring products such as salmon calcitonin, human calcitonin, porcine calcitonin, eel calcitonin and chicken calcitonin, but also analogs such as [$Asu^{1,7}$]-eel calcitonin elcatonin, a product of Toyo Jozo Company, Ltd., as well. Similarly, LH-RH for use herein includes not only the naturally occurring product but also the pharmaceutically active derivatives and analogs thereof such as described in various patents and publications referenced hereinabove, e.g., Matsuzawa et al U.S. Pat. No. 3,917,825. Especially preferred polypeptides for use in the present invention include calcitonin, insulin, ACTH, LH-RH, PTH, CGRP, somatostatin and somatomedin. Calcitonin is the most preferred.

Biodegradable synthetic polypeptides include poly-(N-hydroxyalkyl)-L-asparagine, poly-(N-hydroxy-alkyl)-L-glutamine, copolymers of N-hydroxyalkyl-L-asparagine and N-hydroxyalkyl-L-glutamine with other amino acids.

Definitions or further description of any of the foregoing terms and phrases are well known in the art and may be found by referring to any standard biochemistry reference text such as "Biochemistry" by Albert L. Lehninger, Worth Publishers, Inc. and "Biochemistry" by Lubert Stryer, W. H. Freeman and Company, both of which are hereby incorporated by reference.

The amount of the biologically active peptide in the drug delivery system of the present invention will vary, depending upon the particular polypeptide employed, but will be an amount sufficient to elicit the desired pharmacological effect. Thus, for example, when the selected polypeptide is calcitonin, such will be present in an amount sufficient to treat a condition such as Paget's disease or hypercalcemia or osteoporosis. A typical preparation may contain, for example, from about 0.01 to about 0.04 I.U./mg for porcine calcitonin. In the case of insulin, an amount sufficient to control blood sugar levels and thus to treat diabetes will typically be employed; in the case of LH-RH or analog thereof, an amount sufficient to treat diabetes will typically be employed; in the case of LH-RH or analog thereof, an amount sufficient to treat various disorders of the female reproductive system, an amount sufficient to have a contraceptive effect, or an amount sufficient to elicit any other known biological response to LH-RH will be used, in the case of PTH, CGRP, somatomedin or analog thereof, an amount sufficient to treat various disorders of bone metabolism will be used; and so on for the other biologically active peptides contemplated by the present invention. Thus, the amount of protein or polypeptide useful in the drug delivery system of the present invention is an amount sufficient to achieve the desired therapeutic effect. For guidance, reference may be made to any standard reference text such as Goodman and Gilman, *The Pharmacological Basis of Therapeutics*.

In order to improve the properties and appearance of the drug delivery system of the present invention, one or more excipients, coloring agents, isotonic agents, antioxidants, and the like, may be added to the drug delivery system, for example, excipients such as starch, dextrin, mannitol, sorbitol, cyclodextrin and tragacanth, coloring agents such as beta-carotene, red color No. 2 and blue color No. 1, isotonic agents such as sodium chloride and glucose, and antioxidants such as ascorbic acid and erythorbic acid and their salts or esters. Actual methods of preparing such dosage forms are known or will be apparent, to those skilled in the art. For example, see *Remington's Pharmaceutical Sciences*, 17th edition, 1985, ed. Alfonso R. Gennaro, Mack Publishing Company, Easton, Pa. 18042.

The nature of the excipient(s) will preferably aid in the manufacture of the dosage form selected. Certain dosage forms provide a more extended release of the biologically active protein or polypeptide. These extended release dosage forms are particularly useful and offer increased flexibility in the administration of the protein or polypeptide.

An important feature of the present invention is the fact that there is a physical interaction between the hydrophobic biodegradable polymer and the protein or polypeptide of the present invention. That physical interaction may be characterized as an affinity or as some type of association or interaction between the polymer and the protein/polypeptide.

The physical interaction or adsorption is not clearly understood but it may be characterized somewhat by what it is not. The interaction does not appear to be chemical in nature, i.e., it is not a covalent bond, hydrogen bond or the like. This deduction is on the basis of Differential Scanning Calorimetry, Infrared Spectroscopy, Fourier Transform Infrared Spectroscopy, Raman Spectroscopy and Fourier Transform Raman Spectroscopy. While not wishing to be bound by any theory, the present inventor believes that the -interaction is hydrophobic in nature and involves the amino acid chain linkages. Briefly, it may be depicted as an equilibrium mechanism:

Calcitonin+Polymer⇌Calcitonin-Polymer

Such a mechanism would allow for incorporation of the protein or polypeptide into the polymer matrix as well as allowing its release from the matrix when localized in a body compartment in which the released protein or polypeptide diffuses from the site.

The drug delivery system of the present invention may be prepared by any procedure which allows for the formation of a physical interaction between the hydrophobic biodegradable polymer and the protein or polypeptide. Two such processes may be referred to as the polymer precipitation technique or the microsphere technique.

Figure 1:
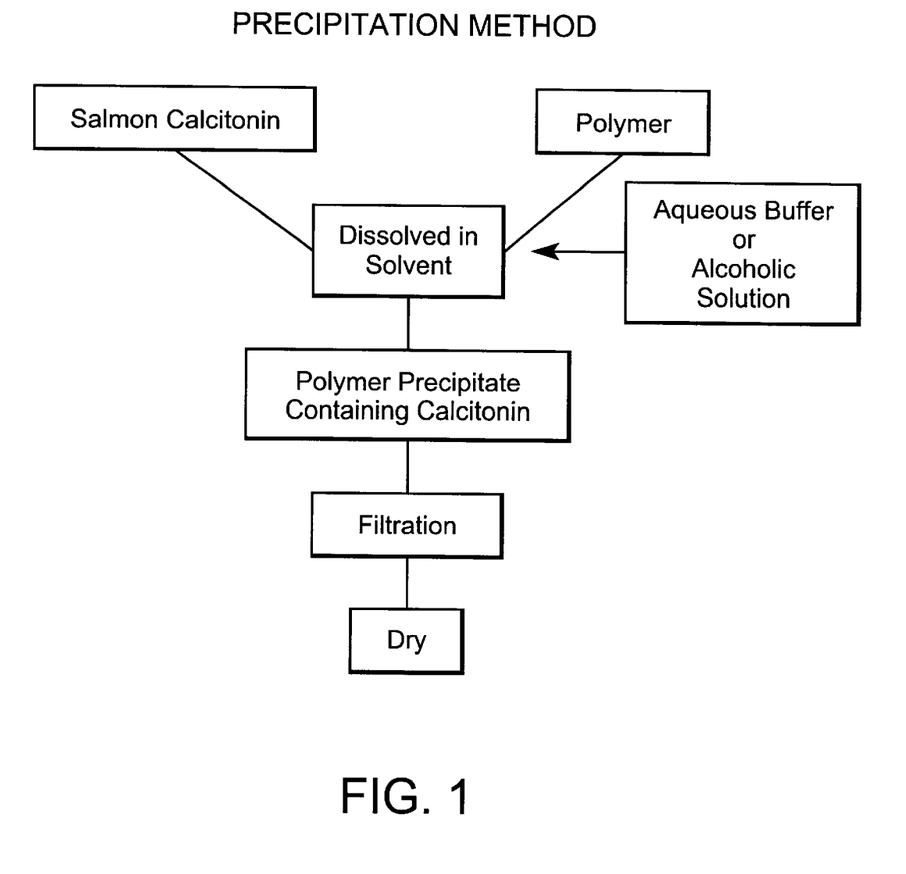
FIG. 1 is a description of the precipitation method of preparing the drug delivery system of the present invention.

In the polymer precipitation technique, the polypeptide and polymer are mixed together with a suitable solvent to form a homogeneous liquid state as depicted in FIG. 1.

Any organic or inorganic solvent may be used as long as both the polypeptide and polymer are soluble in the solvent and the solvent does not degrade or adversely affect the polymer or the polypeptide.

Suitable solvents include but are not limited to methylene chloride, hexafluoroacetone, hexafluoroisopropanol, acetonitrile, hexane, cyclohexane and the like.

The preferred solvents are methylene chloride, hexafluoroacetone and hexafluoroisopropanol.

A precipitate is thus obtained by forcing the polymer and protein/polypeptide out of the solution. The precipitation may be achieved by any technique known in the art. Suitable techniques include adding a solvent in which the polymer is not soluble or cooling the solution to achieve precipitation.

The preferred precipitation technique involves forcing the polymer out of solution using a solvent in which the protein/polypeptide is soluble but in which the polymer is not soluble. Suitable solvents include water, aqueous buffer, aqueous-alcoholic mixtures and the like. Under the proper conditions of stirring, the particle size of the precipitate can be controlled. The precipitate is then filtered and dried.

The precipitate includes both protein/-polypeptide and polymer and a physical interaction is present between the protein/polypeptide and polymer. Controlled release of the protein/polypeptide in vivo is thereby achieved.

Figure 2:
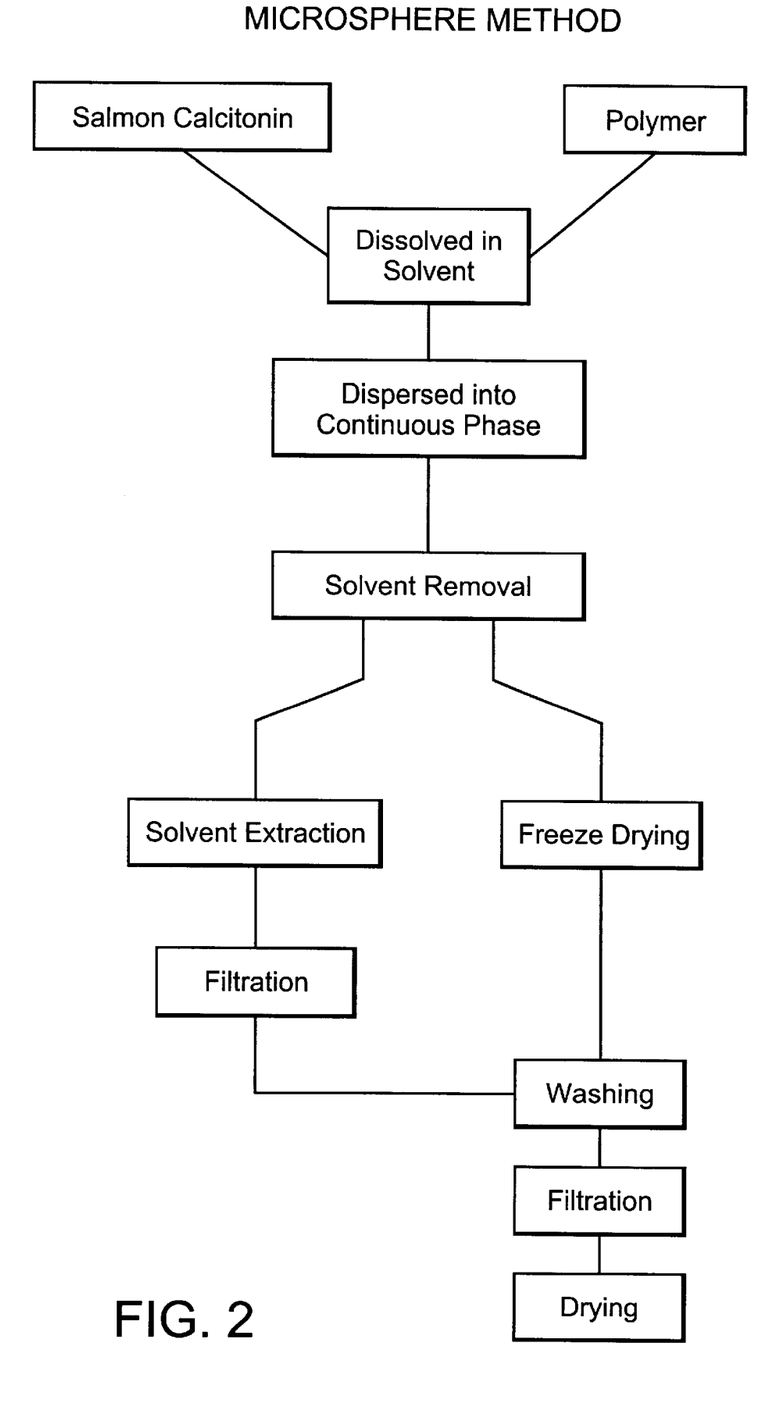
FIG. 2 is a description of the microsphere method of preparing the drug delivery system of the present invention.
Figure 3:
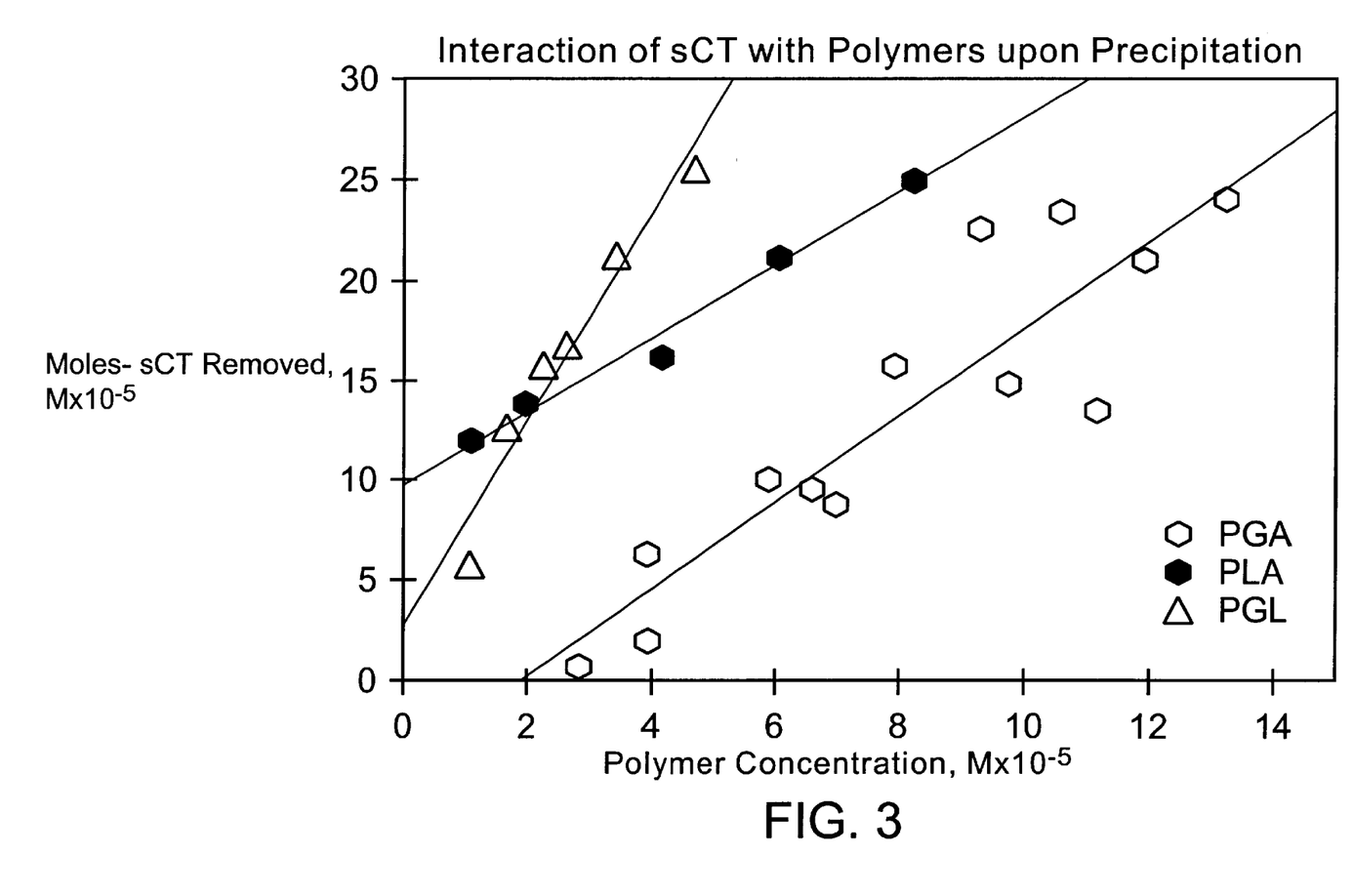
FIG. 3 is a graph depicting the interaction of salmon calcitonin (sCT) with polyglycolic acid, polylactic acid and copolymers of glycolide and L-lactide at varying molar concentrations of polymer.
Figure 4:
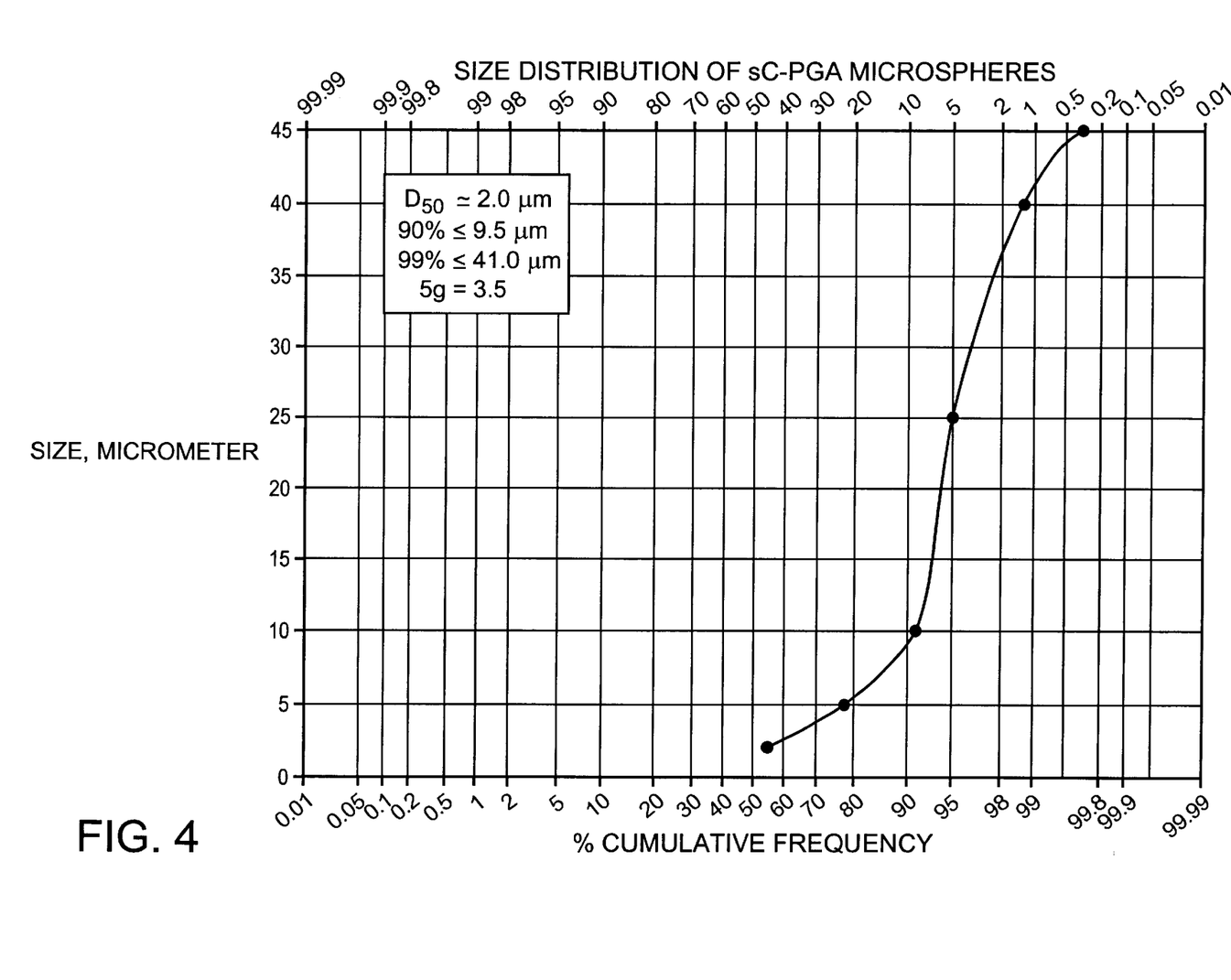
FIG. 4 is a graph of the size distribution of salmon calcitonin and polyglycolic acid microspheres.

If the microsphere technique is used as depicted in FIG. 2, spherical polymer matrices or microspheres having a diameter range between about 1 to 150 microns ($\mu$m) can be prepared in narrow size ranges for targeting to various organ or organ systems via parenteral injection or inhalation as shown in FIG. 4. A more preferred range for the spherical polymer matrices of microspheres is between about 0.5 to 70 microns.

The microspheres may be prepared by forming emulsified droplets or spheres consisting of a homogeneous mixture of polymer (or copolymer) and solvent from a solution of a preselected polymer dispersed in a continuous (non-solvent phase). Removal of the solvent from the sphere by any one or combination of (1) freeze drying, or (2) solvent extraction creates the microsphere. The protein or polypeptide may then be added.

In particular, in the microsphere method, the desired polymer or copolymer and the protein or polypeptide and other agents(s) are dissolved separately in a suitable solvent. The polymer and polypeptide solution are mixed together to provide a polymer concentration generally ranging between about 2.5 to 18% w/w and a polypeptide/polymer ratio ranging between about 1:1 to 1:100. The temperature of the resultant solution is generally controlled between about 30° to 45° C. The polypeptide-polymer solution comprising the dispersed phase is dispersed into the continuous phase containing a surface active agent at a thermostatically controlled temperature generally in the range of 10° to 20° C. Any surface active agent known in the art would be suitable in the practice of the present invention so long as it does not interfere with the activity or interaction between the polymer and protein/polypeptide. The foregoing may be accomplished by any method known in the art, in particular, by forcing the dispersed phase under pressure through a fine orifice nozzle. The continuous phase which is 5 to 20 times by weight of the dispersed phase is then agitated by a dispersator. Following the introduction of the dispersed phase, one of two recovery methods is utilized to stabilize and recover the drug-loaded microspheres for final processing.

More specifically, consistent with the freeze-dry method, following dispersion, the temperature is maintained at 10° to 20° C., preferably 15° C., for two minutes then increased to 45° to 55° C., preferably 50° C., over a three minute period. Vigorous agitation of the mixture is continued during this period. When the temperature reaches 50° C., either a refrigerant solution is circulated through the jacket from the bath or the container is immersed in dry ice-methanol and cooled to a temperature which will freeze the drug-polymer-solvent phase and not the continuous phase. The suspension or emulsion (solid dispersion phase in liquid continuous phase) is quickly transferred to precooled vials (−40° to −60° C.) and cooled to −40° to −60° C. in a freeze dryer, freezer or dry ice-acetone bath. The solvent in the suspended droplets (microspheres) and the continuous phase solvent are removed by freeze drying. Upon completion of the freeze dry cycle the microspheres are washed with a suitable solvent, filtered and air dried.

In the solvent extraction method of the invention, following dispersion, the temperature is maintained at 10° to 20° C., preferably 15° C., for two minutes, then increased to 45° to 55° C., preferably 50° C., over a three minute period. The dispersion is then transferred to a vessel containing a diluent solvent at room temperature or the diluent solvent is added to the dispersion. Agitation may be continued for approximately 30 minutes using an appropriate mixing technique. During the process the dispersed phase solvent is removed from the polypeptide-polymer-solvent emulsion droplets by extraction causing solidification of the droplets. The solid spheres are then removed by filtration, washed with a suitable solvent and air dried.

Solvents for the dispersed phase and the continuous phase will of course differ in order to attain phase separation and are, therefore, selected based upon the solvent requirements for each phase. More particularly, the solvent for the dispersed phase should preferably dissolve the polymer and the incorporated agent and remain in the emulsified droplets with the drug and polymer in the continuous phase until leached out by a diluent solvent or removed by vaporization or evaporation. In this way pores are optionally formed in the drug-polymer matrix. In the case of polyglycolic acid into which water soluble markers or agents are incorporated, hexafluoroacetone sesquihydrate is an appropriate solvent. Other solvents which can be used, depending upon the characteristics of the polymer and incorporated agents, include water, hexafluoro-isopropanol, methylene chloride, acetonitrile, tetrahydrofuran, hexane and benzene. Solvents for the continuous phase should not dissolve the polymer and should emulsify the dispersed phase. Suitable solvents include, but are not limited to, benzene, dioxane, acetone, methylene chloride, chloroform, carbon tetrachloride, toluene, ethyl alcohol, acetonitrile, p-xylene, tetrahydrofuran, mineral oil, glycerin and mixtures of these solvents.

A diluent (non-solvent) phase can also be employed to dilute the continuous phase following dispersion of the polymer polypeptide solution. The diluent should be miscible with the continuous phase and dispersed phase solvents but not dissolve the polymer or incorporated agent. Examples of suitable solvents include 1,4-dioxane, cyclohexanone, acetone, ethanol, isopropanol, acetonitrile, dimethylformamide, tetrahydrofuran, cyclohexanol and the like.

The concentration of polymer in the dispersed phase directly influences the porosity or "void" space in the final microsphere product as well as the shape of the microsphere. A concentration of 2.5% to 10% w/w polymer yields dimensionally suitable spherical particles. With respect to the concentration of the protein or polypeptide, up to 50% by weight of the polymer has been achieved with consistent results.

It has been determined that certain processing parameters influence the recovery methods as well as the resultant microspheres of the present invention. Identifiable parameters include the concentration of polymer in the dispersed phase, the temperature of the dispersed phase at the time of dispersion, the concentration of surfactants in the dispersed phase as well as the ratio of incorporated agent to polymer in the dispersed phase. It will be appreciated that the concentrations, temperatures and ratios referred to hereinabove and in the Examples set forth operable ranges and that other numerical expressions may apply as different solvents, polymers, proteins, polypeptides and the like, are selected.

The present inventor wishes to emphasize that the interaction between the protein/polypeptide and the polymer of the present invention is unique. In the prior art, there was no affinity between the active drug substance and the polymer. In fact, in some instances, the affinity of the drug was much greater for the solvent in which the polymer and drug were dissolved. Thus, in the prior art systems, when the polymer was precipitated from the solution, the drug remained predominantly in the solution.

The drug delivery systems in accordance with the present invention are ideally suited for administration by the parenteral (e.g., intravenous, intraarterial, intramuscular, subcutaneous or intraocular) or inhalation routes of administration but can be used for oral and intranasal administration if such administration enhances bioavailability or reduces side effects. In particular, the macroparticulate systems in the proper size range, i.e., about 0.5 $\mu$m to about 5 $\mu$m, can also be administered orally for adsorption and/or pinocytosis by the mucosal cells lining the gastrointestinal tract. Such administration permits transfer of the incorporated agent intact to the systemic, lymphatic and secretory systems of the body.

It will be appreciated by those skilled in the art that the drug delivery system of the present invention may be administered alone or in admixture with appropriate pharmaceutical diluents, carriers, excipients or adjuvants suitably selected with respect to the intended route of administration and conventional pharmaceutical practices. For example, for parenteral injection, dosage unit forms may be utilized to accomplish intravenous, intramuscular or subcutaneous administration, and for such parenteral administration, suitable sterile aqueous or non-aqueous solutions or suspensions, optionally containing appropriate solutes to effectuate isotonicity, will be employed. Likewise for inhalation dosage unit forms, for administration through the mucous membranes of the nose and throat or bronchiopulmonary tissues, suitable aerosol or spray inhalation compositions and devices will be utilized.

Consistent with other preferred embodiments of the present invention, the drug delivery system of the invention may be additionally coated or modified to advantageously influence the targeting of the release of the incorporated drug therein to preselected target cells, tissues or organs. For example, the drug delivery microspheres may be coated with various agents, e.g., polymers, proteins, surfactants, antibodies or receptor site specific drugs which may be the same or different from those incorporated in the microsphere whereby the release of the incorporated drug is concentrated at the targeted system. Additionally, the coatings can be pH sensitive so as to effect protection following oral administration and transit through the stomach.

In order further to illustrate the present invention and the advantages thereof, the following specific examples are given, it being understood that same are intended only as illustrative, not limitative.

EXAMPLE 1

Molecular Interaction of Salmon Calcitonin with Polyglycolic Acid

The present example was intended to quantify chemical and/or physical association between salmon calcitonin and polyglycolic acid (PGA) having a molecular weight of 40,000 Daltons.

Approximately five mg of calcitonin were quantitatively weighed and placed in each of a series of 5 ml volumetric flasks. Hexafluoroacetone sesquihydrate (HFA) was added dropwise until the calcitonin dissolved completely. A 5% PGA in HFA solution was quantitatively added dropwise to each flask to provide a mass of PGA covering the range of 0 to 26.3 mg. The flasks were agitated for 5 minutes to mix the solution. Each flask was then filled to the 5 ml mark with phosphate buffer (pH 7.3). The addition of buffer precipitated the PGA plus any calcitonin that had bound with the polymer. The resulting mixture was centrifuged and the supernatant was analyzed spectrophotometrically for salmon calcitonin content. 26 mg of PGA (40,000 Mw) removed approximately 4.1 mg (83%) of salmon calcitonin. The results are set forth in Table I.

TABLE I

| PGA MASS (mg) | SUPER-NATANT ABS (275 nm) | CALCITONIN CONC. (mg/ml) | CALCITONIN REMOVED (mg) | % CALCITONIN REMOVED |
|---|---|---|---|---|
| 0.00 | 0.390 | 1.020 | 0.099 | 1.90 |
| 5.73 | 0.342 | 0.895 | 0.125 | 2.71 |
| 7.81 | 0.285 | 0.746 | 1.07 | 22.3 |
| 7.89 | 0.356 | 0.932 | 0.340 | 6.80 |
| 11.8 | 0.213 | 0.558 | 1.71 | 38.0 |
| 13.2 | 0.257 | 0.673 | 1.64 | 32.7 |
| 14.0 | 0.220 | 0.576 | 2.02 | 41.2 |
| 15.8 | 0.176 | 0.461 | 2.69 | 53.7 |
| 18.4 | 0.086 | 0.226 | 3.87 | 77.4 |
| 10.4 | 0.165 | 0.432 | 2.54 | 54.0 |
| 21.0 | 0.068 | 0.175 | 4.10 | 82.1 |
| 22.3 | 0.161 | 0.422 | 2.95 | 58.6 |
| 23.7 | 0.105 | 0.276 | 3.62 | 72.4 |
| 26.3 | 0.066 | 0.174 | 4.13 | 82.6 |

EXAMPLE 2

Molecular Interaction of Salmon Calcitonin with Poly(Glycolic-Co-Lactic Acid)

The procedure of preparing the poly(glycolic-Co-lactic acid) (PGL) having a molecular weight of 50,000 microspheres was similar to that used for PGA, except the hexafluoro-2-propanol was substituted for HFA. Above 8 mg of PGL over 80% of salmon calcitonin was removed. The results are set forth in Table II.

TABLE II

| PGA MASS (mg) | SUPER-NATANT ABS (275 nm) | CALCITONIN CONC. (mg/ml) | CALCITONIN REMOVED (mg) | % CALCITONIN REMOVED |
|---|---|---|---|---|
| 0.00 | 0.360 | 0.941 | 0.591 | 11.1 |
| 2.64 | 0.306 | 0.801 | 0.995 | 19.9 |
| 4.13 | 0.210 | 0.550 | 2.15 | 43.9 |
| 5.52 | 0.191 | 0.501 | 2.69 | 51.8 |
| 6.51 | 0.147 | 0.386 | 2.87 | 59.8 |
| 8.45 | 0.065 | 0.172 | 3.64 | 80.8 |
| 11.53 | 0.047 | 0.125 | 4.37 | 87.5 |
| 13.57 | 0.027 | 0.0725 | 4.44 | 92.5 |
| 20.97 | 0.034 | 0.0908 | 4.95 | 91.6 |

EXAMPLE 3

Molecular Interaction of Salmon Calcitonin with Polylactic Acid

The procedure for preparing the polylactic acid (PLA), dl-type having a molecular weight of 50,000, was similar to that used for PGA, except that methylene chloride was substituted for HFA and the calcitonin was suspended rather than dissolved in the methylene chloride. In addition, since methylene chloride and buffer are not miscible, salmon calcitonin was extracted from methylene chloride in buffer. The aqueous phase was separated, centrifuged and the supernatant was analyzed spectrophotometrically for salmon calcitonin. The results are set forth in Table III.

TABLE III

| PGA MASS (mg) | SUPER-NATANT ABS (275 nm) | CALCITONIN CONC. (mg/ml) | CALCITONIN REMOVED (mg) | % CALCITONIN REMOVED |
|---|---|---|---|---|
| 0.00 | 0.401 | 1.05 | 0.055 | 1.03 |
| 2.68 | 0.226 | 0.592 | 2.04 | 40.8 |
| 4.81 | 0.186 | 0.488 | 2.36 | 47.2 |
| 10.28 | 0.147 | 0.386 | 2.77 | 55.4 |
| 14.95 | 0.105 | 0.276 | 3.62 | 72.4 |
| 20.40 | 0.159 | 0.417 | 3.02 | 60.3 |

EXAMPLE 4

Molecular Interaction of Salmon Calcitonin with Pure Polymer

Approximately 100 mg of PGA (Mw 40,000) was placed in a vial. Ten ml of a 1 mg/ml calcitonin in phosphate buffer (pH 7.3) were added to the vial. The polymer was suspended in the calcitonin solution by placing the vial in an ultrasonic bath for 10 minutes. The suspension was then centrifuged and the supernatant was analyzed spectrophotometrically. This procedure was repeated for PGA (MW 100,000), PGL and PLA (dl-type) polymers, with the revision that all quantitative amounts were halved for the PGL and PLA trials. The results are set forth in Table IV.

TABLE IV

| POLYMER | MASS (mg) | SUPER-NATANT ABS (275 nm) | CALCITONIN REMOVED (mg) | mg SCT per mg POLYMER REMOVED |
|---|---|---|---|---|
| PGA (40,000) | 99.1 | 0.4022 | 0.723 | 0.723/99.1 |
| PGA (100,000) | 99.3 | 0.3501 | 1.143 | 1.143/99.3 |
| PGL (50,000) | 50.0 | 0.4144 | 0.457 | 0.457/50.3 |
| PLA (dl-type) (50,000) | 50.0 | 0.2474 | 2.772 | 2.772/50.0 |

The pure polymers showed a binding affinity, up to 5.5%, which was less than the molecular interaction during the precipitation process. PLA (dl-type) showed the highest affinity to bind with salmon calcitonin when suspended in a 1 mg/ml solution.

Since the PGA system was the polymer of choice for preparing microspheres by the freeze drying technique, some efforts were made to determine the nature of the association between drug and polymer. Utilizing differential scanning calorimetry there was some shifts in the melting points of salmon calcitonin and PGA when these agents were combined in microspheres. Changes were also observed in the I.R. and Raman spectra. All of these suggest an association but do not conclusively point to the precise nature of the interaction. However, Fourier Transfer Raman spectrometry did not show any discernible differences. This suggests that the interaction is not chemical or covalent in nature.

EXAMPLE 5

Preparation of a Salmon Calcitonin-PGA Precipitated System

1. Precipitation with Water 49.3 mg of salmon calcitonin was placed in a vial and dissolved with 0.35 ml HFA sesquihydrate. A 4.5 g of a 10% PGA-HFA solution containing 450 mg of PGA was added dropwise to the solution while stirring with a magnetic stirring bar. The mixture was agitated for 5 additional minutes. A pH 7.3 phosphate buffer was then added to the mixture to precipitate the polymer. Turbidity suggested the precipitation of the polymer. The mixture was agitated two more minutes using a vortex mixer and then centrifuged for 10 minutes at 3000 rpm. The supernatant was saved for analysis and the precipitate dried in a low pressure chamber for a few hours. The salmon calcitonin of the content of the supernatant was analyzed spectrophotometrically and the amount of the active agent removed by the polymer was calculated. Loading was between 6.0 to 8.0% by weight of polymer.

2. Precipitation with Ethyl Alcohol

The buffer was replaced by ethanol to precipitate the polymer to attempt to improve the yield. The total solid input (polymer+salmon calcitonin) was 502 mg in this preparation. A loading of 6.4 to 8.0% was used.

EXAMPLE 6

Characterization of Salmon Calcitonin-PGA Microspheres and Precipitate

1. Blank Microspheres a) Drug Load

Microspheres were prepared as described in Example 5 using 100,000 molecular weight polyglycolic acid. Because of the association tendency of salmon calcitonin with polyglycolic acid, it was not possible to use the precipitation technique to determine actual drug load. The 30 minute extraction technique in buffer was more indicative of actual salmon calcitonin content. By the extraction method and HPLC analysis, a drug content of 8.21 % w/w was calculated as 82% incorporation efficiency.

b) In Vitro Release of Salmon Calcitonin

Figure 5:
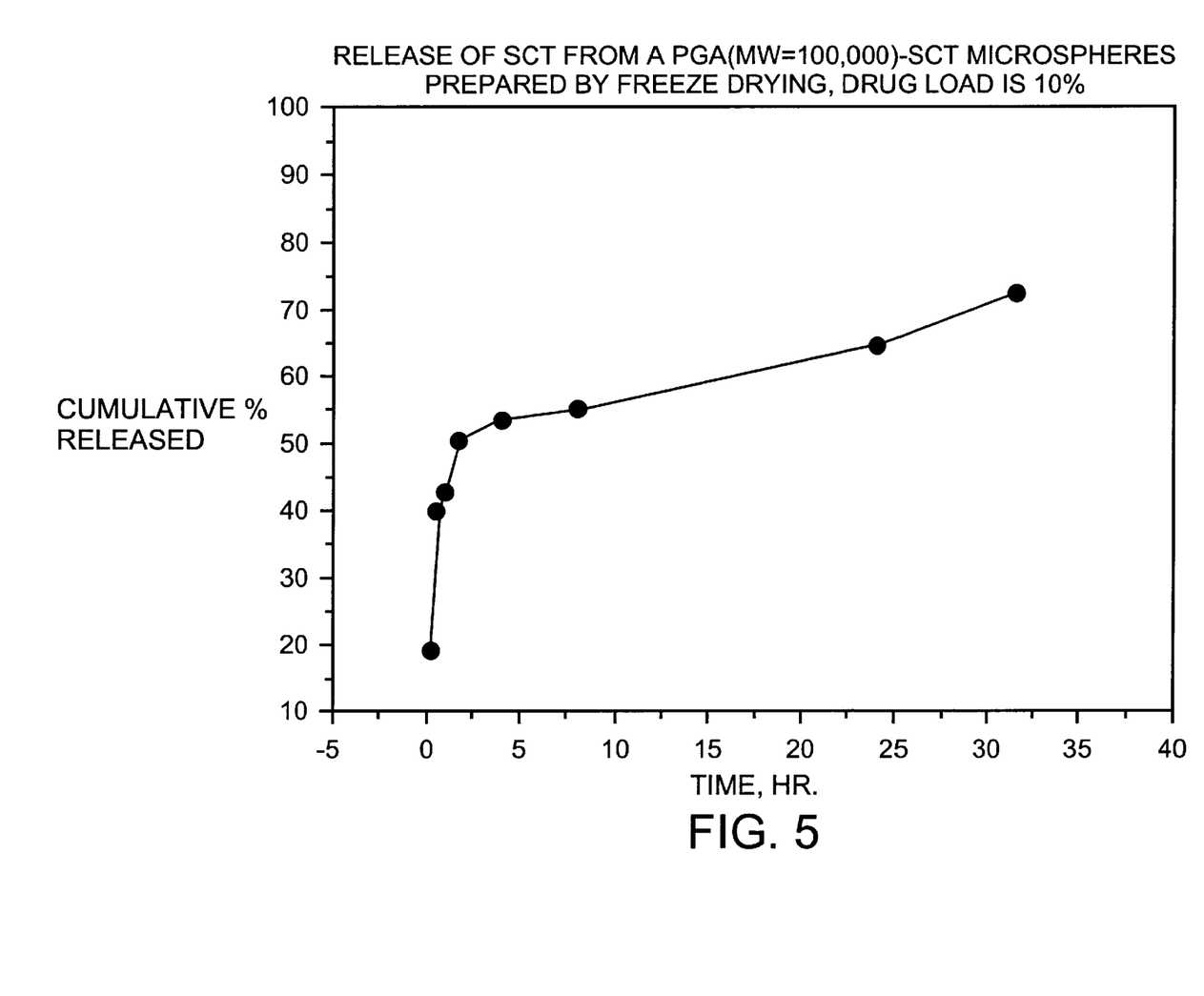
FIG. 5 is a graph of the release of salmon calcitonin from polyglycolic acid Mw=100,000 and salmon calcitonin microspheres prepared by freeze drying. The targeted drug load was 10%.

Twenty mg of PGA-salmon calcitonin microspheres were loaded into a test tube. Ten ml of a 0.1M phosphate buffer, pH 7.4, containing EDTA were added and the tubes transferred to a 37° C. water bath. Results of this study are shown in FIG. 5. Nineteen $\mu$g salmon calcitonin/mg microspheres were released initially as a burst. This initial release was followed by a fast release of 50% of the total drug in less than two hours. At this point, a slow release followed and 22 $\mu$g salmon calcitonin/mg microspheres (22% of total drug) was released in the following 29 hours. The data from this study suggested that salmon calcitonin remains stable in the phosphate buffer for about 35 hours.

2. Precipitate a) Size Distribution

HIAC/ROYCO counter-size analyzer was used to analyze the drug loaded precipitate for size distribution. As shown in FIG. 2, $D_{50}$, the number median diameter, was approximately 2.8 $\mu$m and 99% of the particles were in the range of 2–10 $\mu$m. The geometric standard deviation, σg=1.83 is indicative of a fair monodispersity. MMD, mass median diameter, was calculated to be 4.39 $\mu$m.

b) In Vitro Release of Salmon Calcitonin from Precipitate

Figure 6:
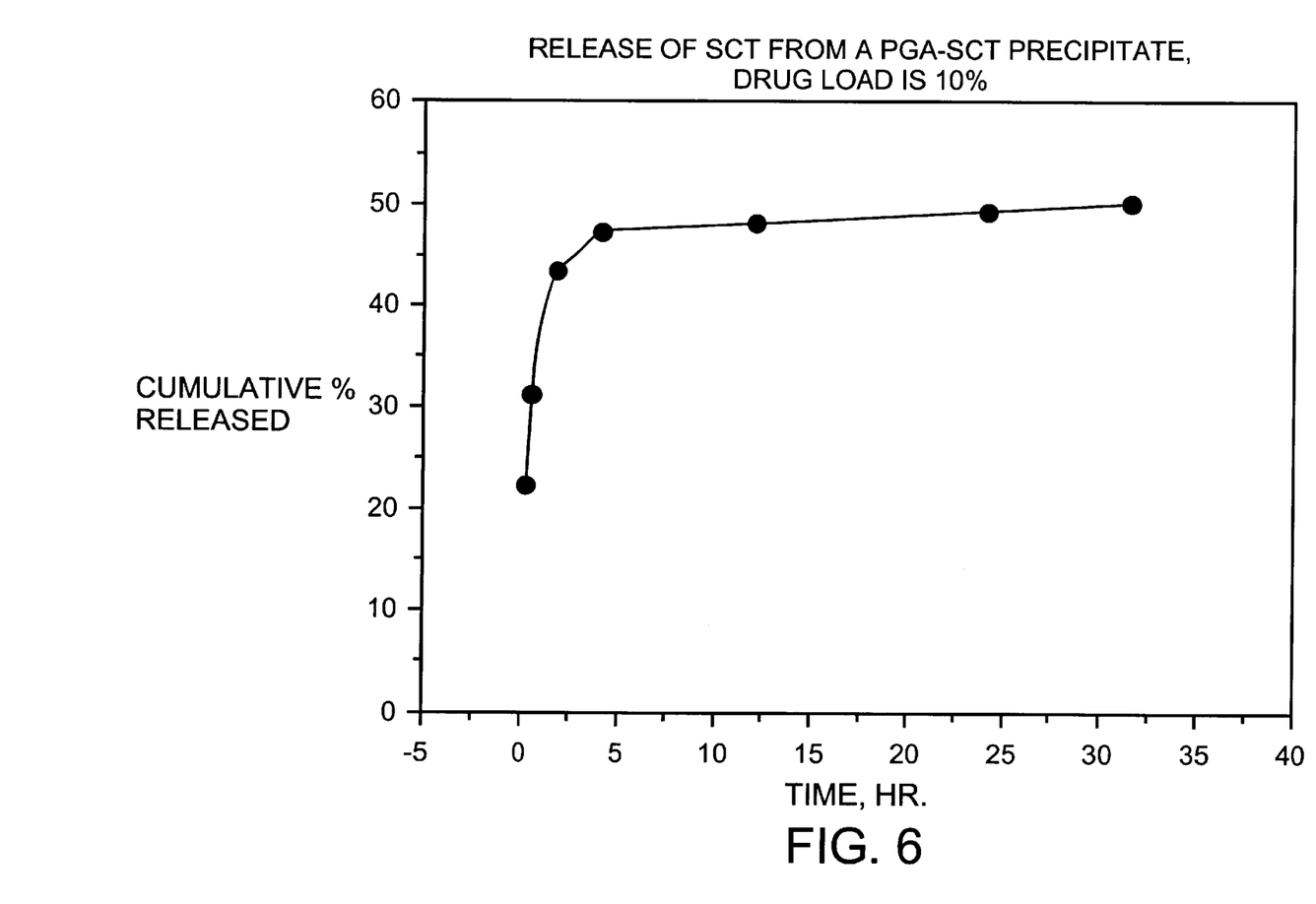
FIG. 6 is a graph of the release of salmon calcitonin from a polyglycolic acid-salmon calcitonin precipitate. The targeted drug load was 10%.

Two 18 mg samples of salmon calcitonin-PGA precipitate were quantitatively transferred to test tubes. Ten ml of a 0.1M phosphate buffer, pH 7.4, containing EDTA were added to the samples and placed in a 37° C. shaker bath. Samples were withdrawn at predetermined time intervals and analyzed for drug content. As shown in FIG. 6, the initial release was rapid. A release of 22% occurred at zero time, followed by another 21% of the total drug released in less than 2 hours. This was followed with only negligible release for the next 30 hours of about 0.1% per hour. A significant amount of salmon calcitonin appears to be still within the matrix or bound to the polymer.

EXAMPLE 7

Figure 7:
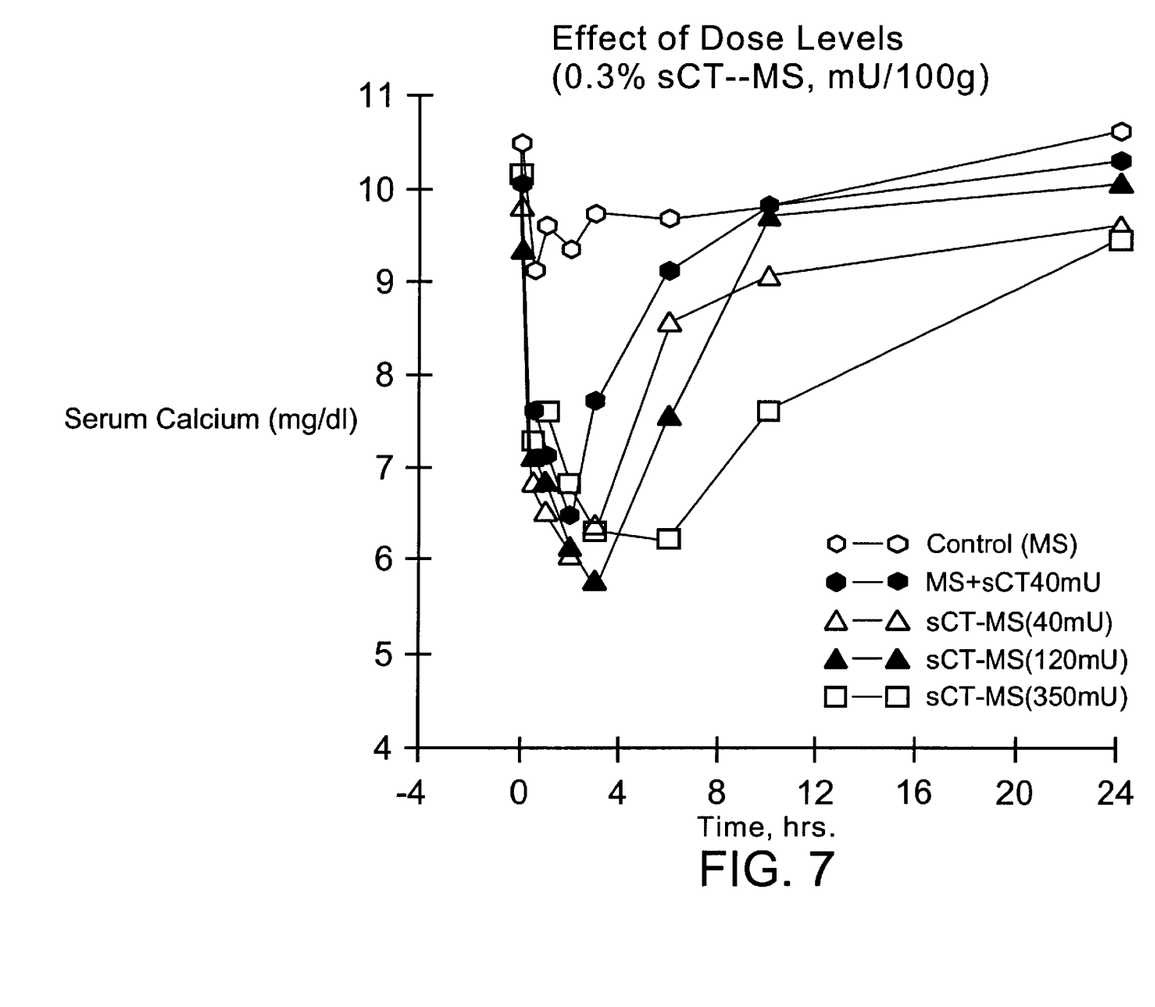
FIG. 7 is a graph of the serum calcium concentration over time of a salmon calcitonin/microsphere drug delivery system.

In Vivo Assessment of Salmon Calcitonin Sustained Release From Biodegradable Microspheres Biodegradable microspheres containing salmon calcitonin were prepared with polyglycolic acid, 40,000D by a freeze-drying technique as depicated in FIG. 2. Salmon calcitonin microspheres with different salmon calcitonin contents were characterized for particle size, porosity, specific surface area and in- vitro release. The sustained hypocalcemic effect was assessed by subcutaneous injection in male Wistar rats, followed by blood sampling via femoral artery catheter at defined time intervals and assaying for serum calcium concentrations. Drug loads of 0.3, 4.5 and 7.5% were evaluated and a level of 0.3% was found to be effective in producing a sustained hypocalcemic effect. With this drug load, salmon calcitonin microspheres containing 40, 120 and 360 mU of salmon calcitonin per 100 g body weight were administered as illustrated in FIG. 7. The hypocalcemic effect was sustained for a 24 hour period with the salmon calcitonin microspheres as compared to 2 to 3 hours with free salmon calcitonin. Additionally, salmon calcitonin blood levels were sustained at concentrations higher than baseline for a period of five days.

From the foregoing description, one of ordinary skill in the art can easily ascertain the essential characteristics of the instant invention, and without departing from the spirit and scope thereof, can make various changes and/or modifications of the invention to adapt it to various usages and conditions. As such, these changes and/or modifications are properly, equitably and intended to be within the full range of equivalence of the following claims.

What is claimed is:

1. A drug delivery system for controlled release of calcitonin, said delivery system comprising a biodegradable hydrophobic polymer selected from the group consisting of polyglycolic acid, polylactic acid, copolymers of glycolic acid and L- or D,L-lactic acid, and copolymers of glycolide and L- or D,L-lactide; and calcitonin, wherein calcitonin is adsorbed to the polymer and a hydrophobic bond is present between said polymer and calcitonin whereby protection and controlled release of calcitonin is achieved in vivo.

2. A process for preparing a drug delivery system for controlled release of calcitonin, said process comprising:

(a) dissolving calcitonin and a hydrophobic biodegradable polymer selected from the group consisting of polyglycolic acid, polylactic acid, copolymers of glycolic acid and L- or D,L-lactic acid, and copolymers of glycolide and L- or D,L-lactide, in a first solvent and dispersing the solution in a second solvent to form microdroplets, (b) extracting the first solvent from the microdroplets, such that an interaction occurs at the aqueous polymer interface causing the calcitonin to adsorb to the polymer, and hardening the polymer such that calcitonin-loaded microspheres are formed.

3. A process for preparing a drug delivery system for controlled release of calcitonin, said process comprising:

(a) dissolving calcitonin and a hydrophobic biodegradable polymer selected from the group consisting of polyglycolic acid, polylactic acid, copolymers of glycolic acid and L- or D,L-lactic acid, and copolymers of glycolide and L- or D,L-lactide, in a first solvent, and (b) adding a second solvent in which calcitonin is soluble, causing the polymer to precipitate and form microparticles to which calcitonin is adsorbed.

4. The process as claimed in claim 2, wherein the microspheres are reduced in size.

5. The process as claimed in claim 3, wherein the microparticles are reduced in size.

6. A process as claimed in claim 3 wherein said second solvent is selected from the group consisting of water, aqueous buffer and aqueous-alcoholic mixture.

7. A process for preparing a drug delivery system for controlled release of calcitonin, said process comprising:

a) dissolving calcitonin and a hydrophobic biodegradable polymer selected from the group consisting of polyglycolic acid, polylactic acid, copolymers of glycolic acid and L- or D,L-lactic acid, and copolymers of glycolide and L- or D,L-lactide, in a first solvent to form a first phase;

b) dispersing said first phase in a continuous second solvent phase to obtain a suspension, and c) removing said first and second solvents from said suspension by freeze-drying to obtain microspheres containing the calcitonin and polymer.

8. The process as claimed in claim 7, wherein the microspheres are reduced in size.

9. A drug delivery system for controlled release of calcitonin prepared according to the process of claim 2.

10. A drug delivery system for controlled release of calcitonin prepared according to the process of claim 3.

11. A drug delivery system for controlled release of calcitonin prepared according to the process of claim 7.

12. A drug delivery system for controlled release of calcitonin, said delivery system comprising a biodegradable hydrophobic polymer selected from the group consistion of polyglycolie acid, polylactic acid, copolymers of glycolic acid and L- or D,L-lactic acid, and copolymers of glycolide and L- or D,L-lactide; and calcitonin, wherein calcitonin is adsorbed to the polymer and a hydrophobic bond is present between said polymer and calcitonin, and not a covalent bond or hydrogen bond as determined by differential scanning calorimetry, infrared spectroscopy, Fourier transform infrared spectroscopy, Raman spectroscopy and Fourier transform Raman spectroscopy, whereby protection and controlled release of calcitonin is achieved in vivo.

13. A process for preparing a drug delivery system for controlled release of calcitonin, said process comprising:

(a) dissolving calcitonin and a hydrophobic biodegradable polymer selected from the group consisting of polyglycolic acid, polylactic acid, copolymers of glycolic acid and L- or D,L-lactic acid, and copolymers of glycolide and L- or D,L-lactide, in a first solvent and dispersing the solution in a second solvent to form microdroplets, (b) extracting the first solvent from the microdroplets, such that an interaction occurs at the aqueous polymer interface causing the calcitonin to adsorb to the polymer and form a hydrophobic bond, and hardening the polymer such that calcitonin-loaded microspheres are formed.

14. A process for preparing a drug delivery system for controlled release of calcitonin, said process comprising:

(a) dissolving calcitonin and a hydrophobic biodegradable polymer selected from the group consisting of polyglycolic acid, polylactic acid, copolymers of glycolic acid and L- or D,L-lactic acid, and copolymers of glycolide and L- or D,L-lactide, in a first solvent, and (b) adding a second solvent in which calcitonin is soluble, causing the polymer to precipitate and form microparticles to which calcitonin is adsorbed, wherein a hydrophobic bond is present between said polymer and calcitonin.

15. A process for preparing a drug delivery system for controlled release of calcitonin, said process comprising:

a) dissolving calcitonin and a hydrophobic biodegradable polymer selected from the group consisting of polyglycolic acid, polylactic acid, copolymers of glycolic acid and L- or D,L-lactic acid, and copolymers of glycolide and L- or D,L-lactide, in a first solvent to form a first phase;

b) dispersing said first phase in a continuous second solvent phase to obtain a suspension, and c) removing said first and second solvents from said suspension by freeze-drying to obtain microspheres containing the calcitonin and polymer, wherein calcitonin is adsorbed to the polymer and a hydrophobic bond is present between said polymer and calcitonin.

* * * * *